United States Patent [19]
Jackson et al.

[11] Patent Number: 5,213,619
[45] Date of Patent: May 25, 1993

[54] PROCESSES FOR CLEANING, STERILIZING, AND IMPLANTING MATERIALS USING HIGH ENERGY DENSE FLUIDS

[76] Inventors: David P. Jackson, 22328 W. Barcotta Dr.; Michael A. Lepp, 22334 W. Barcotta Dr., both of Santa Clarita, Calif. 91350

[21] Appl. No.: 443,471

[22] Filed: Nov. 30, 1989

[51] Int. Cl.$^5$ .............................................. B08B 3/12
[52] U.S. Cl. .................................. 134/1; 204/157.15; 204/158.2
[58] Field of Search ............ 134/1; 204/157.15, 158.2, 204/32.1, 141.5, 131

[56] References Cited
U.S. PATENT DOCUMENTS

| | | | |
|---|---|---|---|
| 4,710,233 | 12/1987 | Hohmann | 134/1 |
| 4,944,837 | 7/1990 | Nishikawa | 156/646 |
| 5,013,366 | 5/1991 | Jackson et al. | 204/157.42 |

*Primary Examiner*—Peter Chin
*Assistant Examiner*—Dean Nguyen
*Attorney, Agent, or Firm*—Roger Marrs

[57] ABSTRACT

An environmentally safe process for pre-cleaning, sterilizing, preserving, and enhancing performance characteristics of materials used in critical environments with stringent end-product cleanliness and sterilization requirements in a single process using high energy dense fluids. One or more dense fluids are mixed with one or more chemical agents and are simultaneously subjected to a non-uniform electrostatic field and high powered acoustic radiation to remove, in a process called acoustic-electroextraction, deeply recessed contaminants from internal and external surfaces of intricately arranged or formulated materials such as biomaterials, surgical tools, or dental implants. Subsequently, the cleaned materials are than subjected to a high energy dense fluid oxidizing environment to provide for deep material penetration and sterilization and removal of biological contaminants. Finally, the cleaned and sterilized materials may be implanted with chemical agents using an acoustic deposition process to provide for long term preservation. In an alternative embodiment of the present invention, chemical agents may be implanted in materials to provide new and improved material properties such as increased electrical insulation. Finally, the entire process may be performed on materials which are prepackaged in semi-permeable membranes, preventing recontamination of the clean, sterile, or implanted materials.

20 Claims, 11 Drawing Sheets

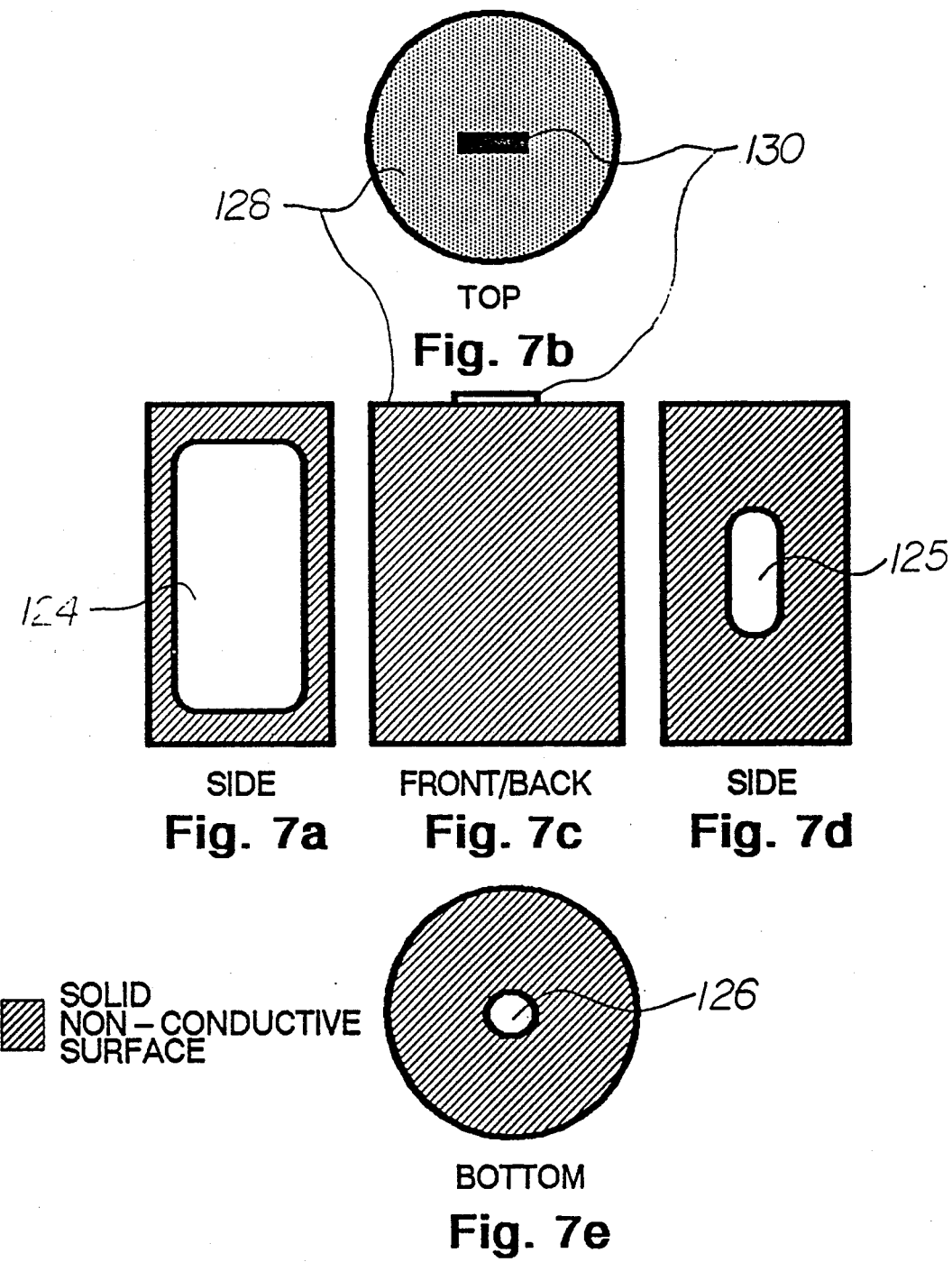

PROCESSES FOR CLEANING, STERILIZING, AND IMPLANTING MATERIALS USING HIGH ENERGY DENSE FLUIDS

BACKGROUND OF THE INVENTION

1. Field of the Invention

The present invention relates generally to the use of liquified and supercritical gases, hereafter described as dense fluids, for cleaning and sterilizing substrates. More particularly, the present invention relates to a process of using sonochemically or electrostatically energized dense fluids or dense fluid mixtures to simultaneously clean and sterilize a variety of inorganic and organic materials, including biomaterials, and to provide a method for impregnating said materials with chemical agents to provide long-term preservation and enhanced performance characteristics.

2. Description of Related Art

Conventional cleaning, sterilization, and preservation processes using hazardous organic solvents, toxic gases, radiation, and topical biocides are currently being re-evaluated due to problems with environmental pollution, toxicity, inefficiency, and/or poor performance. The use of toxic, carcinogenic, or mutagenic substances to achieve sterility have been shown to be deleterious to the environment, pose significant health threats (D. Lynch, et al, "Effects on Monkeys and Rats of Long-Term Inhalation of Ethylene Oxide: Major Findings of the NIOSH Study", AAMI, 1984), require strict control, and create hazardous waste disposal problems. Also, conventional sterilization processes may damage or alter material performance properties. For example, steam autoclaving may greatly accelerate oxide growth on titanium biomaterials (J. Lausmaa, et al, "Accelerated Oxide Growth on Titanium Implants During Autoclaving caused by Fluorine Contamination", *BIOMATERIALS*, Volume 6, January 1985) and must be carefully controlled.

In some cases, the cleaning or sterilizing media chemically reacts with material residues to form harmful by-products. For example, toxic by-products or residual media left in biomaterials following conventional cleaning and ethylene oxide gas sterilization have been shown to adversely impact implant performance (H. Scherer, et al, "Hazards Related to Gas Sterilized Materials, *LARYNG. RHINOL. OTOL.*, 65, 1986). Additionally, conventional biomaterial preparation processes require a separate pre-cleaning operation prior to sterilization operations to assure complete substrate sterility. For example, in ultraviolet (UV) disinfection processes, bacterial shadowing by material structures, cavities, or other contaminants are a great concern (R. Boylan, et al, "Evaluation of an Ultraviolet Disinfection Unit", *THE JOURNAL OF PROSTHETIC DENTISTRY*, Volume 58, Number 5, November 1987). Since ultraviolet treatment is generally only effective on line-of-sight material sterilization applications, complex materials with intricate geometries must be scrupulously cleaned prior to UV sterilization and still may not be suitable candidates for this conventional sterilization process.

Finally, conventional long-term preservation processes are often performed as separate operations, involving immersion of, or application of topical sterilants, disinfectants, and other chemical agents. Several physical and chemical sterilization methods are used in industry. These methods include gamma radiation treatment (Ch. Baquey, et al, "Radiosterilization of Albuminated Polyester Prostheses", *BIOMATERIALS*, Volume 8, May 1987), ultraviolet radiation, steam autoclaving, dry heat, and toxic gas sterilization (*MICROBIOLOGY*, M. Peczar, et al, McGraw-Hill Publishers, 1977, pp 425–423).

Biomedical, aerospace, high energy, and high vacuum materials are fabricated from different types of materials, having various internal and external geometries. These may be assembled biomedical devices such as medical implants, valves, or artificial joints, or they may be surgical aids such as sponges, guidewires, and clips, and may be contaminated with more than one type of inorganic, organic, or biological contaminant. These highly complex materials require pre-cleaning and sterilization processes prior to use in critical environments such as the human body. Often, assembled devices must be disassembled to accommodate conventional cleaning and sterilization processes. Polymeric materials used in surgical applications, or biomaterials, must be free of organic and inorganic residues and microbiological contaminants to provide maximum biologic adhesiveness (cellular adhesion) and no biologic reactivity (Biocompatibility). These polymers must be capable of performing in contact with living tissue and body fluids. This is a highly specialized environment of great biochemical complexity. The principle medical uses of polymers include: structural materials, joint replacements, dental materials, medical devices (including tubing for transport of biofluids both inside and outside the body), adhesives, and sutures. The residual monomers, oils, plasticizers, dyes, pigments, and other additives can produce harmful side effects such as toxic chemical release through bioreaction, infection, swelling, or complete implant rejection.

Because conventional material pre-cleaning and sterilization processes are performed as independent procedures, often the sterilization procedure recontaminates the material with residues or adversely affects the physical properties and subsequent performance of the materials (J. Doundoulakis, D.M.D., "Surface Analysis of Titanium after Sterilization Role in Implant-Tissue Interface and Bioadhesion", *THE JOURNAL OF PROSTHETIC DENTISTRY*, Volume 58, Number 4, October 1987).

Additionally, conventional sterilization processes only deactivate biological contaminants and do not remove these deactivated residues from the material. These residues have been shown to adversely affect the performance of biomaterials following implant operations.

Finally, conventional cleaning and sterilization processes are effective only on external surfaces of composite or intricately arranged materials and provide little or no internal cleaning and sterilization capability.

Accordingly, there is a present need to provide alternate sterilization processes which are suitable for use in removing more than one type of contaminant in complex materials and sterilizing said materials prepackaged in semi-permeable membranes in one continuous process.

SUMMARY OF THE INVENTION

The present invention provides a process for simultaneously cleaning, sterilizing, and preserving materials for use in critical environments such as space, aerospace, manufacturing, biomedical, high energy, or high vacuum. This process provides methods for cleaning complex materials such as composite materials or assemblies of various materials having intricate internal and external geometries. Complex materials may be prepackaged in semi-permeable membranes, cleaned, and sterilized using this process, thus providing long-term protection.

In addition, chemical agents can be implanted in the materials during processing, providing long-term preservation or material property enhancements such as improved conductivity.

Compared to conventional cleaning and sterilizing processes, this invention offers advantages such as no toxicity, environmental compatibility, and in-situ destruction of organic residues.

Finally, the present invention provides an alternative to many conventional cleaning, sterilization, preservation, and packaging processes, often performed as individual steps.

The above-discussed and many other features and other attendant advantages of the present invention will become better understood by reference to the following detailed description when considered in conjunction with the accompanying drawings.

BRIEF DESCRIPTION OF DRAWINGS

FIG. 7a, FIG. 7b, FIG. 7c, FIG. 7d, and FIG. 7e are sectional views of an exemplary rack to be used to load and support the substrates to be cleaned, sterilized, and implanted in accordance with the present invention.

DETAILED DESCRIPTION OF THE INVENTION

In the first embodiment of the present invention, a material containing an undesired substance, such as biological contaminants, on internal or external surfaces, is exposed to a high energy dense fluid environment. The dense fluids suitable for use in the present process comprise either supercritical or liquified gases and chemical admixtures or chemical agents dissolved in the dense fluid or dense fluid mixtures. Unlike conventional solvents such as water, hexane, or carbon tetrachloride, dense fluids exhibit unique chemistry such as variable solvency or solubility for a variety of substances, spontaneous wetting action, and powerful penetrating ability. A dense fluid is a gas or a mixture of gases compressed to supercritical, liquified, or multiphased states to achieve liquid-like densities. The chemistry of dense fluids is well known.

Documented industrial applications utilizing dense fluids include extraction of oil from soybeans (J. Friedrich, et al, "Petroleum-Free Extracts Extracts of Oil from Soybeans", *JAOCS*, Volume 59, Number 7, July 1982), extraction of pyridines from coal (T. Squires, et al, "Supercritical Solvents. Carbon Dioxide Extraction of Retained Pyridine Extracts of Coal", *FUEL*, Volume 61, November 1982), extraction of flavorants from hops (R. Vollbrecht, "Extraction of Hops with Supercritical Carbon Dioxide", *Chemistry and Industry*, 19 June 1982), and regenerating adsorbents (M. Modell, "Process for Regenerating Adsorbents with Supercritical Fluids", U.S. Pat. No. 4,124,528 Nov. 7, 1978)

The gases most suitable for use in the present invention include inorganics such as carbon dioxide, argon, krypton, xenon, nitrous oxide, oxygen, helium, and mixtures thereof. Other gases such as hydrocarbons and halogenated hydrocarbons may serve as cleaning or chemical agent carrier media under normal dense fluid conditions, however these gases will degrade into hazardous by-products in high energy environments and, therefore, are not suitable for use in this invention. Preferably, the suitable gas or gas mixture is preconditioned to remove gaseous impurities such as hydrocarbons, moisture, and microscopic particulates having diameters of 0.2 micrometers or larger.

Figure 1:
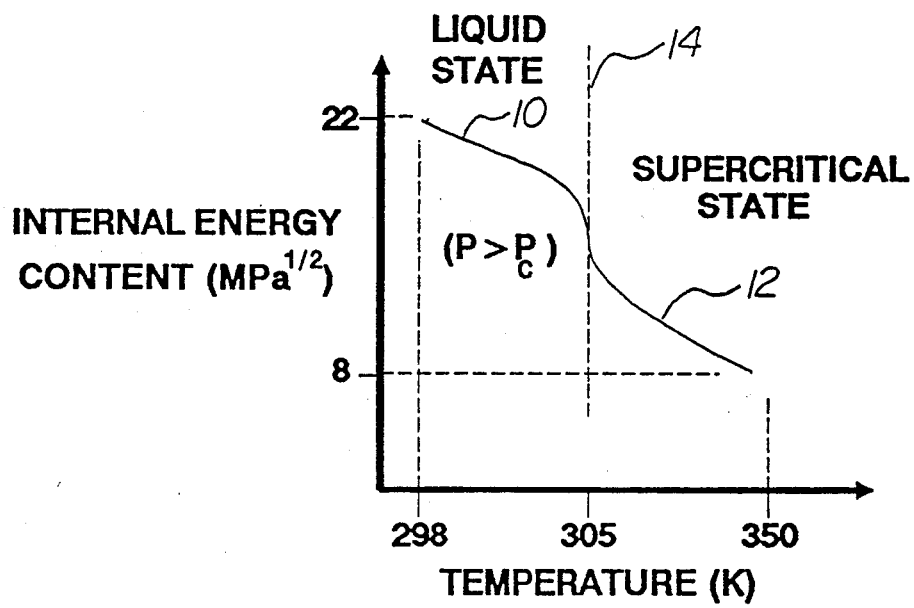
FIG. 1 presents a graph showing the effects of temperature change on dense phase carbon dioxide's internal energy content.

For the precision cleaning, sterilization, and implant phases of the present invention, a dense fluid or dense fluid mixture is chosen to have solubility chemistries, during energizing, which will be compatible with and most effective in dissolving, removing, transporting, or chemically degrading the targeted unwanted residues. Solubility parameters or cohesive energy parameters are used in the present invention to provide a method of correlating and predicting the cohesive energy properties of contaminants, substrates, and dense phase gases or dense fluids. Cohesive energy parameters are used to predict the solubility or maximum cleaning effect of a dense fluid or dense fluid admixture for a particular contaminant or contaminants and maximum penetration effect of a dense fluid or dense fluid admixture for complex solid materials. Several computational methods exist for calculating cohesive energy values for substrates, liquids, and dense fluids (*HANDBOOK OF SOLUBILITY PARAMETERS AND OTHER COHESION PARAMETERS*, A. Barton, CRC Press, 1983). These include the Hildebrand, Hansen, and Giddings equations, among others. FIG. 1 shows the type of solubility spectrum curves for liquid phase 10 and supercritical phase carbon dioxide 12 as a function of temperature at or above the critical pressure generated using the Giddings equation (J.C. Giddings, et al, "High Pressure Gas Chromatography of Nonvolatile Species", *SCIENCE*, 162, 67, 1968) for the supercritical phase and the Hildebrand equation for the liquified carbon dioxide. Subcritical fluid or liquified gas cohesive energy values can be computed using classical Hildebrand calculations based upon readily available vapor pressure data (K.L. Hoy, "New Values of the Solubility Parameters from Vapor Pressure Data", *JOURNAL OF PAINT TECHNOLOGY*, Volume 42, Number 541, February, 1970). Finally, cohesive energy values for solid surfaces or materials with higher than liquid densities can be computed based upon readily available surface tension data (L. Jackson, "Surface Characterization Based on Solubility Parameters", *ADHESIVES AGE*, October, 1976).

Dense phase carbon dioxide is the preferred dense fluid for use in practising the present process as both the cleaning solvent and carrier solvent since it is non-toxic and inexpensive. The critical temperature of carbon dioxide is 305 Kelvin (K) (32 Celcius) and the critical pressure is 72.9 atmospheres (atm) (75 kilograms per square centimeter). The solute carrying capacity, or cleaning qualities of carbon dioxide can be modified by changing its physical and chemical makeup, while remaining at or above its critical pressure. As shown in FIG. 1, increasing the temperature of dense phase carbon dioxide from 298 K (25 degrees celcius) to 350 K (77 degrees celcius) at the critical pressure for carbon dioxide (73 atm) changes the dense fluid internal energy content from approximately 22 $MPa^{\frac{1}{2}}$ to approximately 8 $MPa^{\frac{1}{2}}$. This energy change is accompanied by a change in dense fluid state 14, from liquid phase to supercritical phase, once the critical temperature of 305 K (32 degrees celcius) is reached. This change in internal cohesive energy is accompanied by an overall change in the dipole-dipole solubility properties (solvent spectrum) of dense phase carbon dioxide, excluding hydrogen bonding and polar energy contributions, of which, dense phase carbon dioxide has none. Thus, in accordance with the present invention, the dense fluid or dense fluid mixture (may be modified with polar and hydrogen bonding contributors) is energized to simultaneously produce a spectrum of solvency by creating localized supercritical fluid zones within the subcritical fluid (cavitation sites). In this approach, a variety of contaminants differing in solubility chemistry are provided suitable solvent environments in a single dense fluid or dense fluid mixture. Alternatively, blends of nitrous oxide-carbon dioxide, xenon-carbon dioxide, and argon-carbon dioxide provide enhanced cleaning capability by changing or shifting the solubility chemistry range, hence contaminant selectivity range.

In a second embodiment, materials are prepackaged in semi-permeable membranes, such as TYVEK (a product trademark of E.I. DuPont de Nemours Co.), and processed according to the processes of the present invention. Prepackaged materials have extended shelf-life expectancies, can be handled directly following processing, and are ready for use upon opening, such as in surgical implant applications.

In a third embodiment of the present invention, dense fluid mixtures are simultaneously subjected to intense acoustic and electrostatic energy fields to further enhance cleaning ability. This provides the capability of creating the optimum cleaning solvent environments for dissolving and transporting a range of contaminating residues from material pores and surfaces. The high energy environment employed in the present invention is derived from a high powered variable acoustic radiation source coupled with an ionizing non-uniform electric field. These high energy sources actuate specific physical and chemical changes in the dense fluid or dense fluid mixture chemistries, the material being processed, the unwanted residues, and the chemical agents transported in the dense fluid. This enhances cleaning, sterilization, and preservation of the materials processed.

Figure 2A:
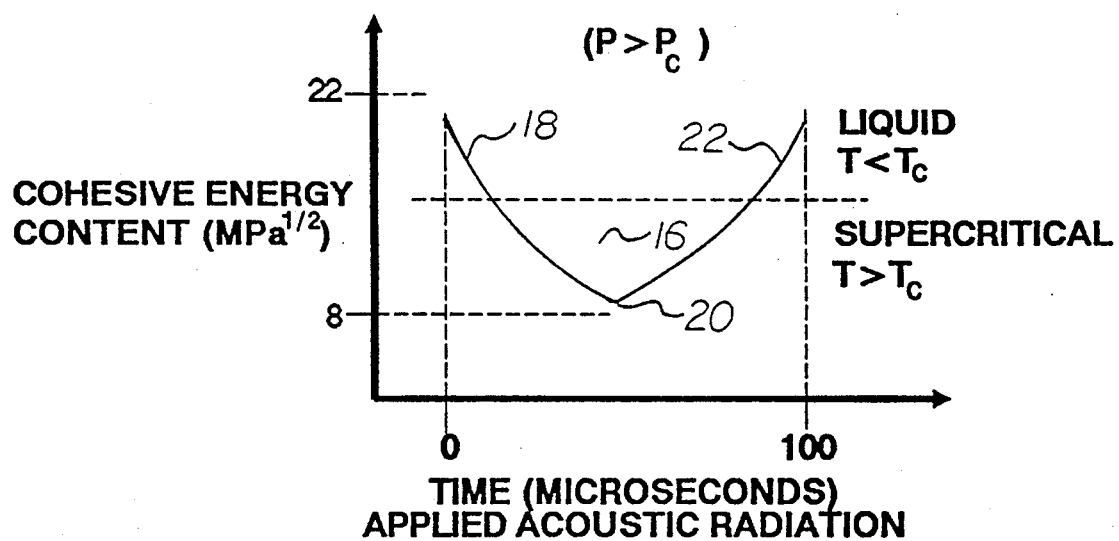
FIG. 2a presents a graph showing the effect of acoustic radiation upon the solubility behavior of dense phase carbon dioxide, measured in terms of cohesive energy content versus time in microseconds of applied acoustic radiation.

Acoustic radiation for practising the present invention is provided by a high-powered ultrasonic generator which converts electrical energy into mechanical energy, or acoustic radiation, via a piezoelectric transducer. The transducer is coupled to a titanium metal surface which transmits the acoustic radiation into a dense medium such as liquids, creating intense high and low acoustic pressure waves. This effect is illustrated in FIG. 2a. As shown in FIG. 2a, intense pressure differentials create supercritical fluid implosion cavities 16 to form, a process called supercritical cavitation in this invention. Thus, in about 100 microseconds, the cavitation site undergoes a change from liquid state 18 to supercritical state 20 and back to liquid state 22 following cavity expansion and implosion cycles (cavitation). This state change is accompanied by an overall cohesive energy change in excess of 10 $MPa^{\frac{1}{2}}$.

Conventional applications of ultrasound include material cleaning using aqueous media such as water-soap solutions, homogenization, cell disruption, degassing fluids, and reaction catalysis (K. Suslick, "The Chemical Effects of Ultrasound", *SCIENTIFIC AMERICAN*, February, 1989). Intense acoustic radiation required for practising the present invention can be produced using a 400 watt variable frequency (20 to 40 kilohertz) titanium horn available from B.Braun Biotech, Inc., Bethlehem, Pa. The acoustic horn is inserted into the cleaning chamber and secured using compression fittings. High energy acoustic radiation is applied during specific material processing cycles of this invention to enhance penetration of dense fluid or dense fluid mixtures into substrate pores, propagation of high energy oxidizing radicals (chemical breakdown), and to enhance removal of a variety of contaminants from deeply recessed pores. During cleaning cycles, wide-range contaminant removal is accomplished via intense pressure differentials created by the acoustic radiation. High and low pressure zones in the dense fluid create supercritical fluid solvent zones having different solubility chemistries. This phenomenon can be explained by examining the sonochemistry of conventional ultrasound applications in standard temperature and pressure (STP) liquids.

When a liquid such as water is acoustically radiated, cavitation will not occur until dissolved gas in the water has been removed. During the first few seconds of acoustic radiation, the gas is forced out of solution by the intense sonic expansion (heating), a process called acoustic degassing. Expanding gas bubbles dampen or absorb acoustic radiation, preventing liquid cavitation from occurring. Thus, if a STP liquid is vaporized easily, it will not cavitate at all. For example, if terpene-based solvents are acoustically radiated, voluminous quantities of terpene vapor are formed. These vapors dampen the acoustic radiation and cavitation is never initiated.

Figure 2B:
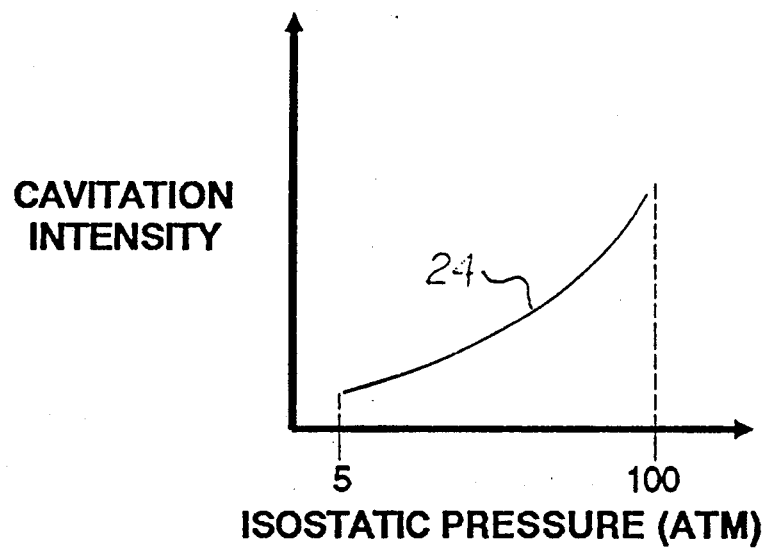
FIG. 2b presents a graph showing the effect of isostatic pressure ($P_o$) on the intensity of acoustic pressure $P_a$) or cavitation energy.

In the present invention, a liquified gas, or mixture of liquified gases and chemical agent admixtures, is acoustically radiated at a pressure above its critical pressure ($P_c$) and below its critical temperature ($T_c$). The dense gas molecules absorb acoustic energy, raising cavitation temperatures above the critical temperature, hence the internal energy content in those regions. Since the liquified gas or gas mixture cannot vaporize under the pressure conditions of the present process, expansion heat creates microenvironments of supercritical fluid in these localized regions. The heat in these regions is rapidly dissipated and re-liquification of the gas occurs. This heating and cooling of the dense fluid to form two phases simultaneously is called multi-phasing in the present invention. If acoustic radiation is continuously applied without internal temperature control, the temperature of the bulk dense fluid will steadily rise above the critical temperature forming a single supercritical fluid phase. Thus a wide range of solvent chemistries are produced using one dense fluid or dense fluid mixture. This effect is controlled to promote decontamination of substrates and for implanting chemical agents into materials. Moderate dense phase gas pressures or isostatic pressures present in this invention enhance the penetration effects of acoustic radiation. FIG. 2b presents a graph showing the general effect of isostatic pressure upon cavitation energy. As shown in FIG. 2b, the cavitation energy increases considerably with isostatic pressure 24. An increase in cavitation energy promotes the penetration of dense fluids into closed-end micro-cavities, such as those commonly found in amorphous polymers. However, acoustic pressure must be maintained between 2 and 4 times that of the isostatic pressure to have the maximum effect. This is done by increasing the power output on the acoustic amplifier to provide additional acoustic pressure on the titanium horn. In the present invention, multi-phasing is controlled by varying the acoustic energy output (acoustic pressure) and by an internal temperature compensator; an externally fed closed-loop water or gas cooled or heated thermal surface located in the processing chamber, which also serves as an electric field/ion collector and cold trap in the present invention. Controlling the acoustic radiation intensity and the temperature compensator creates temperature gradients from the surrounding dense fluid towards the heat sink. The multiphasing process is more pronounced when liquified mixtures of suitable dense fluids are acoustically radiated, for example, nitrous oxide and carbon dioxide or xenon and carbon dioxide. Due to differences between the critical temperatures of the individual mixture components, regions of two-phase-two-component dense fluid are created during acoustic cycles, enhancing the contaminant solubility range, hence the cleaning qualities of the dense fluid mixture. Thus, multiphasing eliminates the need for providing specific compatible solvent-solute environments by simultaneously providing a range of solvent environments in one dense fluid or dense fluid mixture, in one continuous process.

In another feature of the present invention, the internal temperature compensator serves as a contaminant collector or cold trap. The temperature compensator condenses and traps contaminants removed from the material during cleaning and electrostatic thermal-vacuum operations of the present invention, preventing back-transfer or re-deposition of contaminants onto substrate surfaces during acoustic electroextraction cycles and chamber depressurization.

Figure 3:
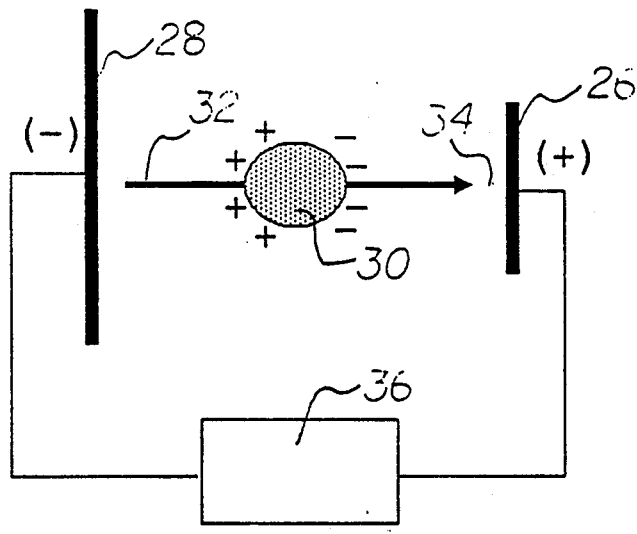
FIG. 3 is a diagram showing the effect of a pulsed non-uniform electric field upon contaminants, particles, and dense fluid molecules.

A non-uniform ionizing electric field employed in the present invention is used to facilitate removal of contaminants from substrates through electrophoretic movement. One effect produced by the non-uniform ionizing field is charge agglomeration of submicron particles and migration of agglomerated contaminants towards a grounded internal collector plate. An exhaust port is located near the grounded plate to facilitate removal of collected contaminants from the cleaning chamber. Another effect produced by the non-uniform electric field is electromigration of concentrated contaminants in internal pores to the more dilute dense fluid surrounding the material being processed, a process called zone electrophoresis. The electric field gradients further enhance cleaning by causing migration of charged ionic contaminants from internal material pores towards the grounded plate. The electric field is pulsed to provide both negatively and positively charged field gradients in the dense fluid and material being processed. FIG. 3 shows the effect of a non-uniform electric field upon contaminants, particles, and dense fluid molecules in a non-uniform electric field. As shown in FIG. 3, the electric field is concentrated 34 near the collector plate 26. This is accomplished by electrostatically charging a field source plate 28, using a pulsed switching electrostatic field generator 36, which is larger than the grounded collector plate 26. This promotes the attraction of both negatively and positively charged species 30, through polarization, towards the collector plate 26, creating an electrostatic field energy field gradient 32. Even neutral particles and chemical species will move in this non-uniform electric field and independent of sign, both negatively and positively charged species will migrate in unidirectional motion in the direction of the concentrated electrostatic field 34. This effect is analogous to sedimentation of particles or macromolecules in a gravitational field. The properties of the dielectric media between oppositely charged plates greatly impacts the electrophoretic mobility of species either dissolved or suspended in the media or the material being processed. Electroextraction media having high dielectric strength and low viscosity maximize electrophoretic mobility or migration velocity in a non-uniform electric field. Scientific formuli used for calculating the electrophoretic mobility of dissolved or suspended species in various media (*BIOCHEMISTRY*, L. Stryer, W.H. Freeman and Co., 1981, p 90) show that high dielectric strength and low viscosity dense fluid media used for practising the present invention provide extremely high contaminant mobilities. Thus, a material suspended in a dense fluid or dense fluid mixture between oppositely charged plates in a non-uniform electric field is purged of various internal contaminants through a process called dense fluid electroextraction in this invention. Contaminants migrate from internal surfaces of the material to the surrounding dense fluid and are either trapped on the internal temperature compensator or they are exhausted from the cleaning chamber during depressurization operations.

An ionizing non-uniform electrostatic field for use in practising the present invention is accomplished by using a charged hemispherical ion/field source emission plate and a hemispherical grounding plate (ion/field collector) on opposite sides of the material being processed. The ion/field emission plate surface is much larger than the collector surface to create the non-uniform electric field density during electrostatic field pulsing operations. A pulsed electrostatic charge of +/−100 to +/−10000 volts per centimeter (volts/cm) of direct current (DC) is applied to the emitter plate. Dense fluid molecules and contaminants are charged or ionized in the electrostatic field and migrate towards the grounded collector plate.

Figure 4A:
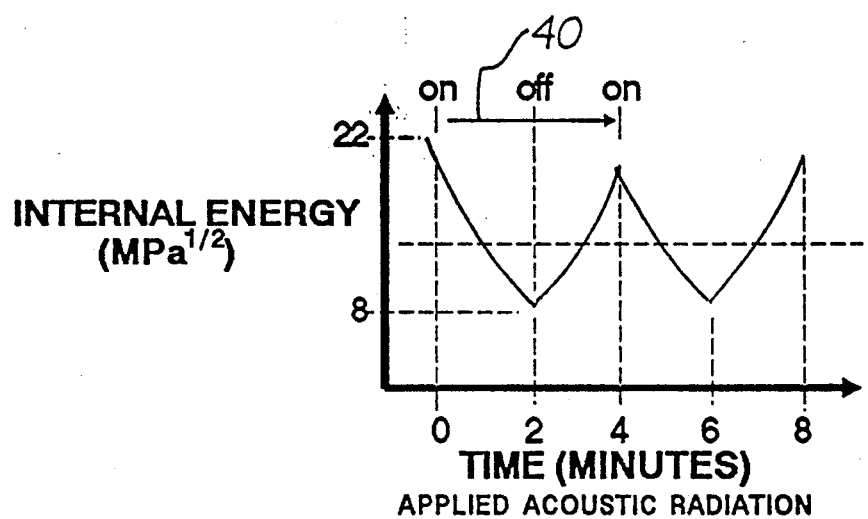
FIG. 4a and FIG. 4b are diagrams illustrating the exemplary acoustic and electrostatic cycling sequences used simultaneously to produce dense phase gas multiphasing and electroextraction cleaning effects in accordance with the present invention.
Figure 4B:
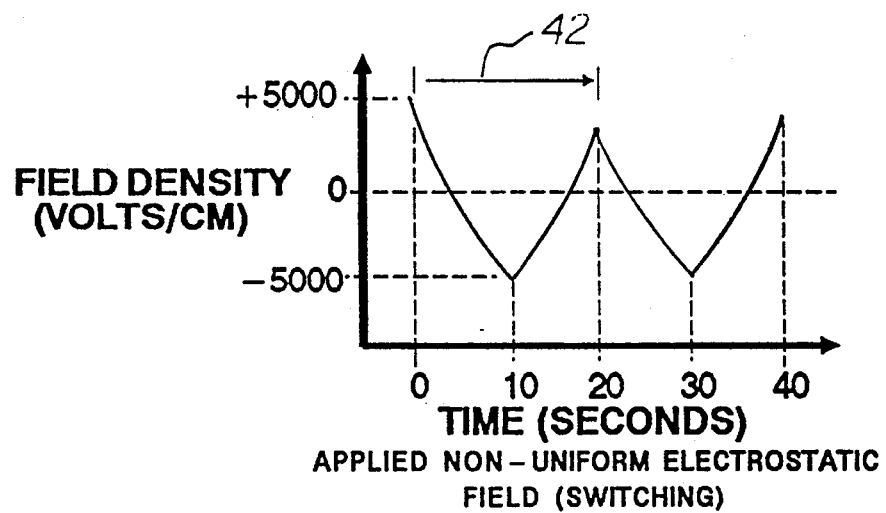

The simultaneous application of acoustic and electrostatic energies creates the high energy environment necessary to precision clean and sterilize intricately arranged or complex materials. Since the acoustic and electrostatic energy effects are propagated through complex materials, these effects are internalized in the materials, promoting rapid decontamination through solubility and electromigration mechanisms described above. FIG. 4a and FIG. 4b illustrate the preferred acoustic and electrostatic sequences respectively, used to produce the high energy multi-phasing environment of the present invention. As shown in FIG. 4a, a pulsed acoustic radiation is applied in on/off cycles 40 over several minutes, in combination with internal temperature control, to alter the overall solubility chemistry of the dense fluid to provide optimum contaminant transport and cleaning conditions for a variety of contaminants and substrates. As shown in FIG. 4b, a pulsed electrostatic field is alternated in both positive and negative charge cycles 42 between +5000 volts/cm DC and −5000 volts/cm DC during the acoustic cycling sequence. The combination of acoustic energy and a non-uniform electrostatic field provides wide-range contaminant solubility and uni-directional contaminant mobility.

In a fourth embodiment of the present invention, chemical oxidizing agents are transported into the cleaning chamber as admixtures with the dense fluid. The dense fluid admixture is then exposed to high energy acoustic electrostatic radiation to create highly energetic oxidizing radicals. This high energy mixture rapidly destroys biological and other organic contaminants which are deeply recessed in the material being processed. Following penetration and oxidation of internal contaminants, oxidation by-products and residues are removed via the dense fluid during chamber depressurization or recharging operations.

Dense fluid chemical agent admixtures or modifiers suitable for practising this embodiment of the present invention include hydrogen peroxide and oxygen, or other chemical agents which will produce oxidizing species or radicals under the high energy conditions employed in the present invention. Alternatively, alcohols, surfactants, biocides, and other chemical agents can be used in combination with the oxidizing agents to enhance the cleaning ability of the dense fluid or dense fluid mixture to remove a specific contaminant or range of contaminants, or provide long-term bactericidal properties if implanted in materials. For example, a liquid carbon dioxide-dimethyl sulfoxide (DMSO) mixture, in combination with a secondary chemical agent, can be injected into the cleaning chamber to promote penetration of the secondary chemical agent into dense materials or the targeted contaminant, for example, biological spores.

Hydrogen peroxide is the preferred chemical agent admixture in practising the cleaning and sterilization operations in the present invention since it enhances dense carbon dioxide's cleaning qualities under both low and high energy conditions, is an excellent biocide, and decomposes into innocuous by-products during high energy decomposition. Hydrogen peroxide is highly soluble in both organic and inorganic matrices, hence it is an excellent penetrating admixture. In addition, unlike carbon dioxide, hydrogen peroxide has a large dipole and low dielectric strength. Thus, a mixtures of carbon dioxide and hydrogen peroxide in varying ratios possess a wide range of hydrogen bonding, polar, and dipole energy contributions, hence solubility chemistries. Carbon dioxide-hydrogen peroxide fluid mixtures have been shown in our research to have remarkable cleaning ability for many organic, inorganic, and ionic residues under the high energy conditions employed. Hydrogen peroxide chemically degrades into highly active atomic oxygen, hydroxyl and hydrogen radicals under the high energy conditions employed in the present invention, rapidly decomposing biological and other organic contaminants into water and gaseous by-products. Thus, hydrogen peroxide serves as a dense fluid solvent modifier, cleaning solvent, oxidant, and biocide in the present invention.

In a fifth embodiment of the present invention, an ionized argon gas environment under conditions of high vacuum (0.0001 Torr) and moderate temperature (60 degrees celcius) is used to enhance removal of volatile contaminants from materials during material preconditioning processes. This process also is used to facilitate removal of residual gas and admixture residues following cleaning and sterilization processes of the present invention. Similar to the aforementioned dense fluid zone electrophoresis, ionized argon gas transfers charge to residual contaminants, raising their energy levels and aiding in volatilizing the ionized contaminants under high vacuum and moderate temperature. The charged contaminants migrate toward the internal grounded cold surface plate. For example, residual moisture, present following dense fluid oxidation operations, is rapidly vaporized when ionized. This ionized vapor is subsequently removed, under high vacuum, from the substrate through electromigration. We have found in our research that the electrostatic thermal vacuum process, as compared to conventional thermal vacuum operations, lowers the temperatures and processing times required to energize and separate volatile contaminants from substrate surfaces.

In a sixth embodiment of the present invention, chemical agents, such as phenols, alcohols, halogens, organometallics, dyes, and detergents, are dissolved in a dense fluid or dense fluid mixture at temperature and pressure conditions which have been optimized, based upon cohesive energy calculations, and are transported into a cleaning chamber, whereupon the said chemical agent or chemical agents are deposited on internal and external material surfaces through a process called acoustic deposition in this invention. In this embodiment, the preferred chemical agents are chosen which, if deposited on internal and external surfaces of the material being processed, provide prolonged enhancements following cleaning and sterilization such as long-term sterility, impart pleasant odor, or improve material performance characteristics such as improved insulation resistance. The chemical agent admixture is deposited onto internal and external surfaces of the material by changing the selectivity or solute carrying capacity of a dense fluid for a particular chemical agent to cause separation of the admixture from the dense fluid and subsequent deposition of chemical agent. This is accomplished via multi-phasing operations. The dense fluid-chemical agent mixture is allowed to contact the substrate for several minutes to assure complete penetration. Following this, the mixture is acoustically radiated without temperature compensation. The bulk fluid mixture temperature rises to non-solvent conditions, with internal energy content dropping below 12 MPa$^{\frac{1}{2}}$, subsequently dropping the chemical agent out of solution, effecting deposition on internal and external surfaces. For example, referring to FIG. 1, the total energy change for dense phase carbon dioxide at the critical point 14 is approximately 10 $MPa^{1/2}$ at the critical pressure of 73 atm. It should be noted that the range for the change in cohesive energy content at the critical point decreases as the operating pressure for the system increases above the critical pressure. For example, if a dense carbon dioxidechemical agent admixture is acoustically radiated at 150 atm and the bulk fluid temperature is allowed to rise to the critical temperature, the total cohesive energy content changes from 22 $MPa^{1/2}$ to 14 $MPa^{1/2}$, or 8 $MPa^{1/2}$. Therefore, in an additional feature of the present embodiment, deposition rates and levels per acoustic cycle can be controlled by varying the isostatic processing pressure in the cleaning chamber prior to or during acoustic cycles.

Alternatively, chemical agents can be implanted in materials according to the processes of the present invention to modify their properties. For example, electrostatic-safe materials can be produced by implanting static electricity dissipative organics such as surfactants.

Thus, high energy sources are employed in the present invention to create, in combination, thermal, acoustic, and electrostatic energy environments and gradients. These energy sources are applied to dense fluids, dense fluid mixtures, and gases under negative pressure in one continuous process to provide optimum cleaning and sterilization conditions for removing a variety of organic and inorganic, ionic, particulate, and biological contaminants.

The necessary processing parameters: gas type, gas mixture ratios, acoustic and electrostatic energy intensities, temperature and pressure, and exposure durations necessary to achieve the desired cleanliness and sterility levels are dependent upon the nature and extent of contamination and the configuration of the material being processed. These parameters can be readily determined experimentally as follows. The material is subjected to the high-energy cleaning and sterilization conditions in accordance with the present invention and then the material is subjected to testing to determine the cleanliness and sterility level achieved. The material may be examined by visual or microscopic inspection or by other more extensive material cleanliness tests such as standard plate count, total mass loss, electrical conductivity, or mechanical and thermal properties. Alternatively, a witness specimen of similar material composition and prepackaged in a semi-permeable membrane may be subjected to various cleaning processing conditions and tested for cleanliness and sterility compliance. For example, a spore strip pre-packaged in TYVEK, available from American Scientific Co., Norwalk, Calif., containing millions of viable bacterial spores may be subjected to the processes according to the present invention and cultured to determine the effectiveness of the processing conditions. From this data, the optimum processing parameters may be determined. With the aid of system and process computerization, these processing parameters are correlated with factors such as material composition and contaminant type(s) to provide a processing library to assist the development of new material applications and to provide consistent cleaning and sterilization of established material applications. As an alternative, in-line chemical analysis instrumentation techniques such as gas chromatography (GC) may be used to examine dense fluid extracts from the chamber as an indicator of material cleanliness.

The material cleaning, sterilization, and preservation processes discussed above are accomplished in three distinct sequences in one continuous process, in accordance with the first, second, third, and fourth embodiments of the present invention. Due to the complexity of the operations involved in these sequences, computerization and automation are required to assure consistent processing of materials. The processing sequences of this invention will be best understood by reference to the following detailed discussion of the cleaning and sterilization components and system integration. A detailed discussion of the processing sequences will follow.

An exemplary cleaning and sterilization system, including computerization and major component integration, for practising the present invention is shown diagramatically in FIG. 5. As shown in the figure, the exemplary cleaning and sterilization system for use in practising the present invention would include a gas supply 44 consisting of one or more of the preferred gases, a gas preconditioning system 46 used for removing trace contaminants in the gas supply, and a chemical injection system 48 for formulating and injecting dense fluid-chemical agent admixtures into the cleaning and sterilization chamber 50. A cleaning and sterilization chamber 50 in which a material is loaded, secured using a rack (not shown), and processed according to this invention, is equipped with internal non-uniform electrostatic field plates 52 and an internal titanium acoustic radiator or horn 54. The electrostatic field plates 52 are powered by an external switching pulsed direct current power supply 56 and the titanium horn is coupled to a transducer 58 and a high powered pulsed variable frequency acoustic generator 60. Finally, a high vacuum pump 62 is connected to the cleaning and sterilization chamber for vacuum electrostatic decontamination processes of the present invention. These major system components are connected using various valves, pumps, and pipes as shown symbolically in FIG. 5 to control dense fluid flow, chemical agent injection, mixing, temperature, and pressure. In addition, the exemplary system has, as a minimum, a temperature sensor 64 and a pressure sensor 66 located at the cleaning and sterilization chamber injection or exhaust ports. Finally, the exemplary cleaning and sterilization system with its network of valves, sensors, pumps, mixers, and high energy systems are integrated with a computer system 68 using an analog-digital controller 70 and computer control software 72. Information such as dense fluid energy calculations and processing parameters in relation to the specific material cleaning and sterilization endproduct requirements would be correlated and stored in material process libraries to provide complete and consistent material processing and would serve as a reference database for new material applications. The entire processing system as described above, excluding the computer system 68 would preferably be housed and operated in an environmental control enclosure (Federal Standard 209B Class 100 Air Quality) (not shown) to prevent re-contamination of materials processed according to this invention.

FIG. 6*a* is a detailed diagram of an exemplary cleaning and sterilization chamber for use in practising the cleaning, sterilization, and preservation processes of the present invention. As shown in the figure, this system includes an injection port 74 used to deliver dense fluids or dense fluid-chemical agent admixtures to the inside 76 of the cleaning and sterilization chamber 78 where the material 80 to be processed in accordance with this invention is secured in a rack 82 and an exhaust port 84 to reduce pressure or to eject contaminants during depressurization, dense fluid-chemical agent recharging, or electrostatic thermal vacuum processing sequences of this invention. The cleaning and sterilization chamber 78 and pin closure 86, used to seal the chamber during processing sequences, as well as all internal high energy system components, are composed of materials capable of withstanding the high energy, temperature, and pressure conditions of the present invention as well as chemically compatible with the suitable dense fluids and dense fluid admixtures used to process materials. The non-uniform electrostatic field used in the present invention is generated by delivering a pulsed DC charge, via an electrical connection and high pressure passthrough 88, to an internal hemispherical ion emitter plate 90 which has a larger surface area than the oppositely charged internal hemispherical ion collector plate 94 on the opposite side of the cleaning and sterilization chamber which is mated to, and heated or cooled by, an external coolant or heating agent delivery system 92 using a closed-loop high pressure thermal coil 96. The smaller hemispherical ion collector plate 94 is connected to the thermal coil 96 so that it serves as an internal temperature compensator, ion collector, and cold trap in accordance with the processes of this invention. A titanium radiator or horn 98 is inserted through the bottom of the cleaning and sterilization chamber 78 and secured to the cleaning chamber 78 using high pressure compression fittings to provide the acoustic energy required to raise internal energy levels and to produce multi-phasing in accordance with the present invention. The titanium horn 98 is coupled to a transducer assembly 110 and to an adjustable high powered variable frequency (20 to 40 kilohertz) generator 102. Finally, the internal surfaces of the cleaning and sterilization chamber 78 are covered or coated with an electrically insulative non-contaminating coating or sleeve such as TEFLON (A registered trademark of E.I. Dupont de Nemours Co.). This helps to control temperature and to minimize electric field loss between the electrostatic field plates. Finally, the external body of the cleaning and sterilization chamber is fitted with a ceramic heating band (not shown) to be used for heating the chamber during electrostatic thermal vacuum cleaning cycles of the present invention.

Figure 6A:
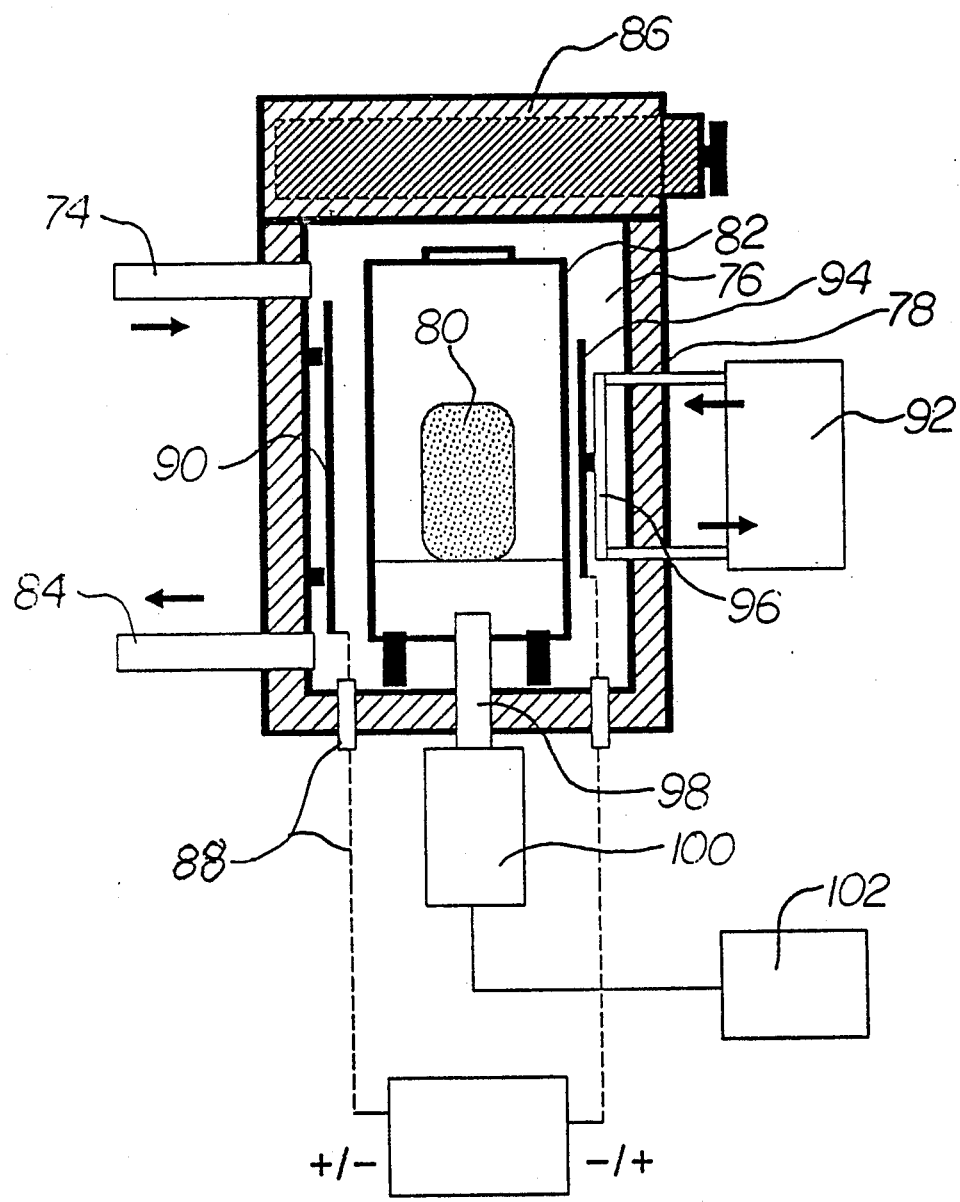
FIG. 6a and 6b are partial sectional views of the preferred exemplary cleaning and sterilization chamber and chemical agent injection system, respectively, for use in accordance with the present invention.
Figure 6B:
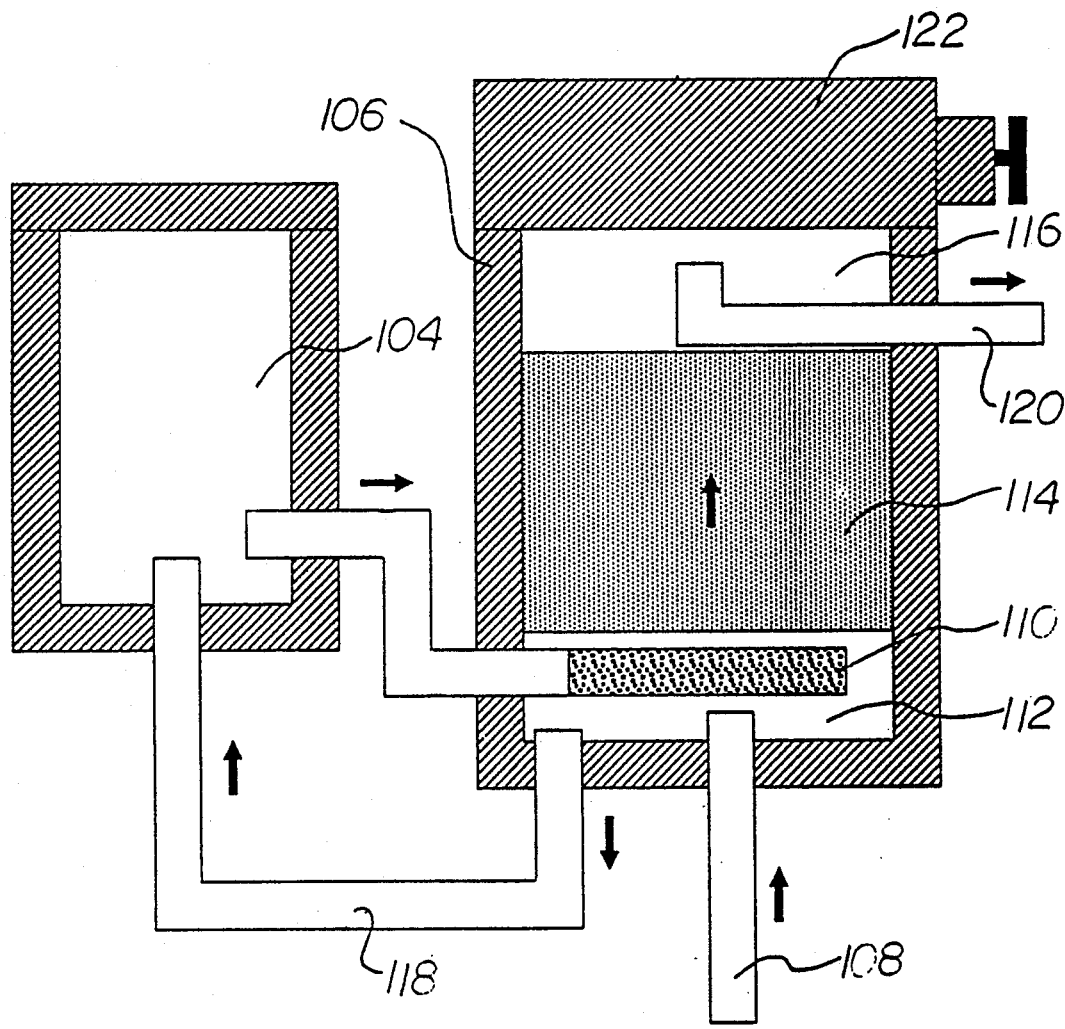

FIG. 6b is a detailed diagram of an exemplary chemical agent injection system for use in practising the sixth embodiment of the present invention. As shown in the figure, the chemical agent injector includes a chemical agent reservoir 104 which contains the chemical agent or mixture of chemical agents to be added to a chemical injection chamber 106 and mixed with suitable dense fluid carrier media, introduced through an injection port 108 which is situated below a chemical agent injection diffuser 110, and then injected into the cleaning and sterilization chamber (not shown). A diffuser assembly 110 is used to disperse the chemical agent(s) into the injection mixing chamber 112 as fine droplets to aid in dissolving a fraction of the chemical agent in the dense fluid carrier. Dense fluids used to clean and sterilize materials are used as carrier solvents and are injected into the injection mixing chamber 112 via an injection port 108, whereupon the dense fluid and chemical agent(s) rise through a column of fine mesh stainless steel scrubbing media 114 or other suitable scrubbing media. The saturated dense fluid-chemical agent admixture rises vertically through the injection chamber into a saturation zone 116 and insoluble chemical agent gravity settles to the bottom of the injection chamber 112 where it is pumped, via the chemical agent return line 118, back into the chemical agent reservoir 104. The saturated dense fluid-chemical agent admixture is then pumped through an exhaust port 120 and into the cleaning and sterilization chamber (not shown). Alternatively, a magnetically driven mixer (not shown) or an acoustic horn (not shown) may be integrated with the injection chamber to assist in dissolving chemical agents with suitable dense fluids in the injection mixing zone 112. In addition, cooling and heating systems such as cooling coils (not shown) and ceramic heating bands (not shown) may be affixed to the external surfaces of the chemical agent injection chamber 106 to provide internal chamber temperature conditions which are most suitable for dissolving the desired fraction of chemical agent into a dense carrier fluid or dense fluid mixture, based upon cohesive energy calculations. The injection chamber is equipped with a pin or bolted closure 122 which allows for periodic opening and cleaning of the injection chamber cavity. All external and internal surfaces and components of the exemplary chemical agent injection system are constructed of materials which are chemically and physically compatible with the pressures, temperatures, suitable dense fluids, and suitable chemical agents used for practising the present invention.

FIG. 7a, 7b, 7c, 7d, and FIG. 7e are sectional schematics of the front, back, top, bottom, and sides of an exemplary rack for loading, securing, and unloading materials in the exemplary cleaning, sterilization, and preservation chamber. As shown in the FIG. 7a and FIG. 7d, the exemplary rack includes openings in the sides to accommodate the different sizes of hemispherical ion emitter plate 124 and ion collector plate 125 (plates not shown) in the cleaning and sterilization chamber (not shown). As shown in FIG. 7e, a spherical opening 126 located at the bottom of the rack allows for insertion and feed through of the titanium horn (not shown). The exemplary loading rack shown here has no shelves, however, suitable loading racks with shelves, designed to be non-obstructive of the acoustic and electrostatic energy sources, can be manufactured which allow for processing of numerous materials simultaneously. It should be noted that many other rack configurations can be developed to accommodate materials having different geometric configurations. Racks should be constructed out of materials which are chemically and physically compatible with the dense fluids, dense fluid-chemical agent admixtures, pressures, temperatures, and high energy conditions present in this invention. As shown in FIG. 7b and FIG. 7c, the top 128 of the exemplary processing rack is constructed of electrically and thermally insulative materials and fits tightly between the electrically insulated cleaning and sterilization chamber walls (not shown). The rack top 128 serves as an electrical and thermal insulator between the chamber closure (not shown) and the hemispherical ion emitter and collector plates (not shown). Finally, as shown in FIG. 7b and FIG. 7c, the exemplary material processing rack has a handle 130 affixed to the top of the rack 128 to assist in loading and unloading the rack and materials from the cleaning and sterilization chamber (not shown).

Figure 8:
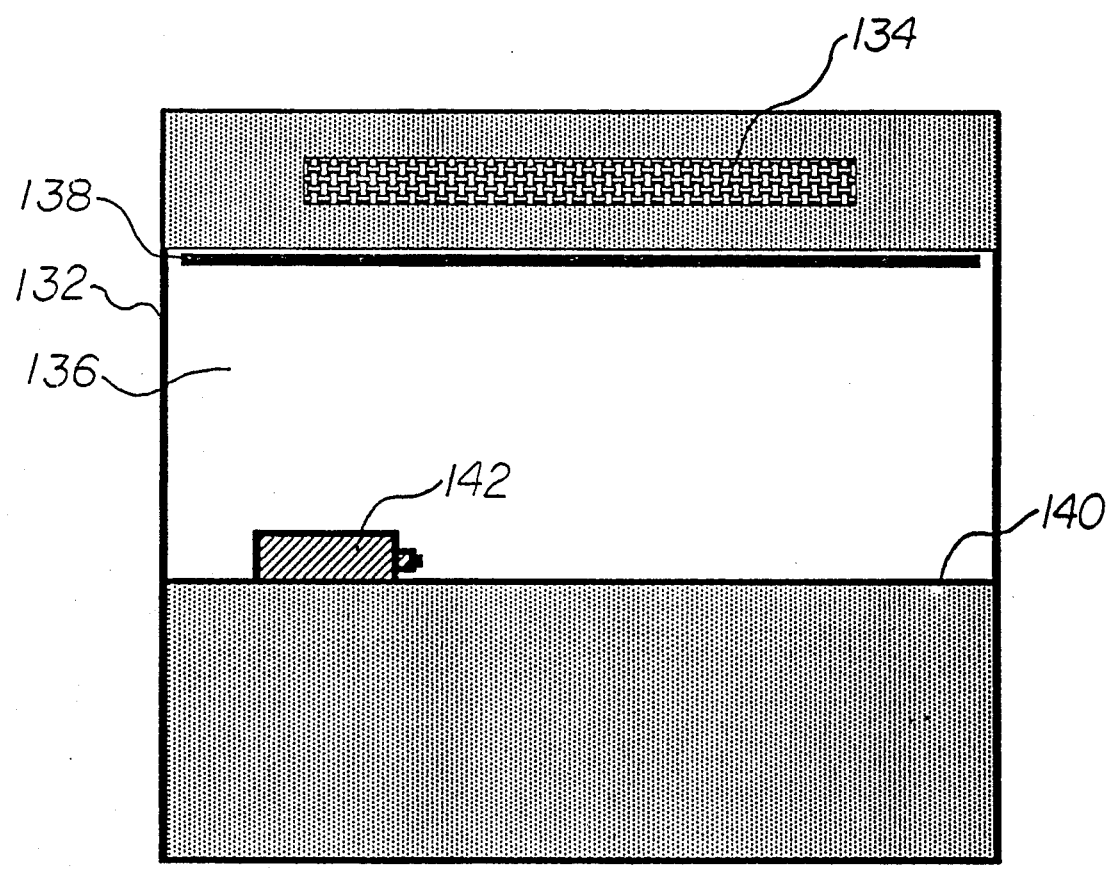
FIG. 8 is a partial sectional view of an exemplary environmental control enclosure used to house the preferred cleaning, sterilization, and implant system and to practice the processes in accordance with the present invention.

FIG. 8 is an exemplary environmental control enclosure used to house the preferred cleaning, sterilization, and preservation system. Following processing of materials in accordance with the present invention, and upon removal of the closure from the cleaning and sterilization chamber, the materials are exposed to the external environment. The processed materials can be contaminated by airborne organic and inorganic contaminants such as vapors and particles if not prepackaged in semipermeable membranes or protected by other techniques. An environmental control enclosure is preferred to house the exemplary cleaning, sterilization, and implant system and to perform the processes of the present invention. The exemplary enclosure protects unpackaged precision cleaned, sterilized, and implanted materials once removed from the cleaning and sterilization chamber from airborne biological, organic, and inorganic contaminants. As shown in FIG. 8, the exemplary environmental control enclosure includes a vertical or horizontal draft laminar flow work bench 132 equipped with a high efficiency particulate (HEPA) filtration system 134 to provide better than 99.9% removal of airborne particulate matter having diameters of 0.25 microns or greater within the interior of the work station 136, and an ultraviolet radiation light source 138 having a principle output radiation wavelength of approximately 253 nanometers to sterilize line-of-sight work surfaces 140. Finally, the preferred integration of the exemplary cleaning and sterilization chamber 142 with the exemplary environmental control enclosure is shown in FIG. 8. A computer control system (not shown) would be located adjacent to or remotely from the environmental enclosure.

Having thus discussed the exemplary cleaning, sterilization, and preservation system components necessary for practising the various embodiments of the present invention, the following is a detailed discussion of the cleaning, sterilization, and implant processes, with appropriate references to the above discussed system components.

Figure 5:
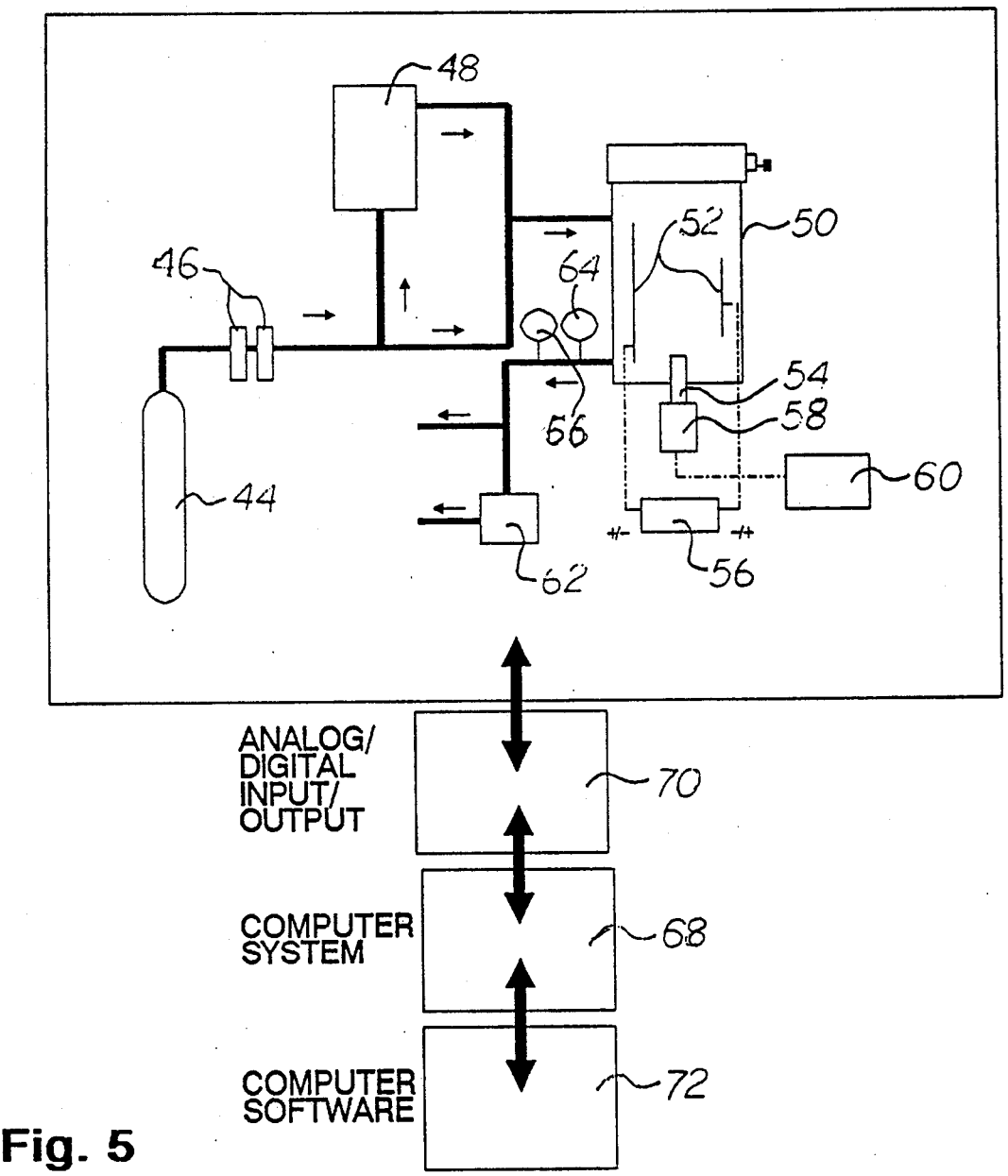
FIG. 5 is a diagram showing the major components and integration of the preferred cleaning, sterilization, and chemical injection systems, including computerization, for use in accordance with the present invention.
Figure 9A:
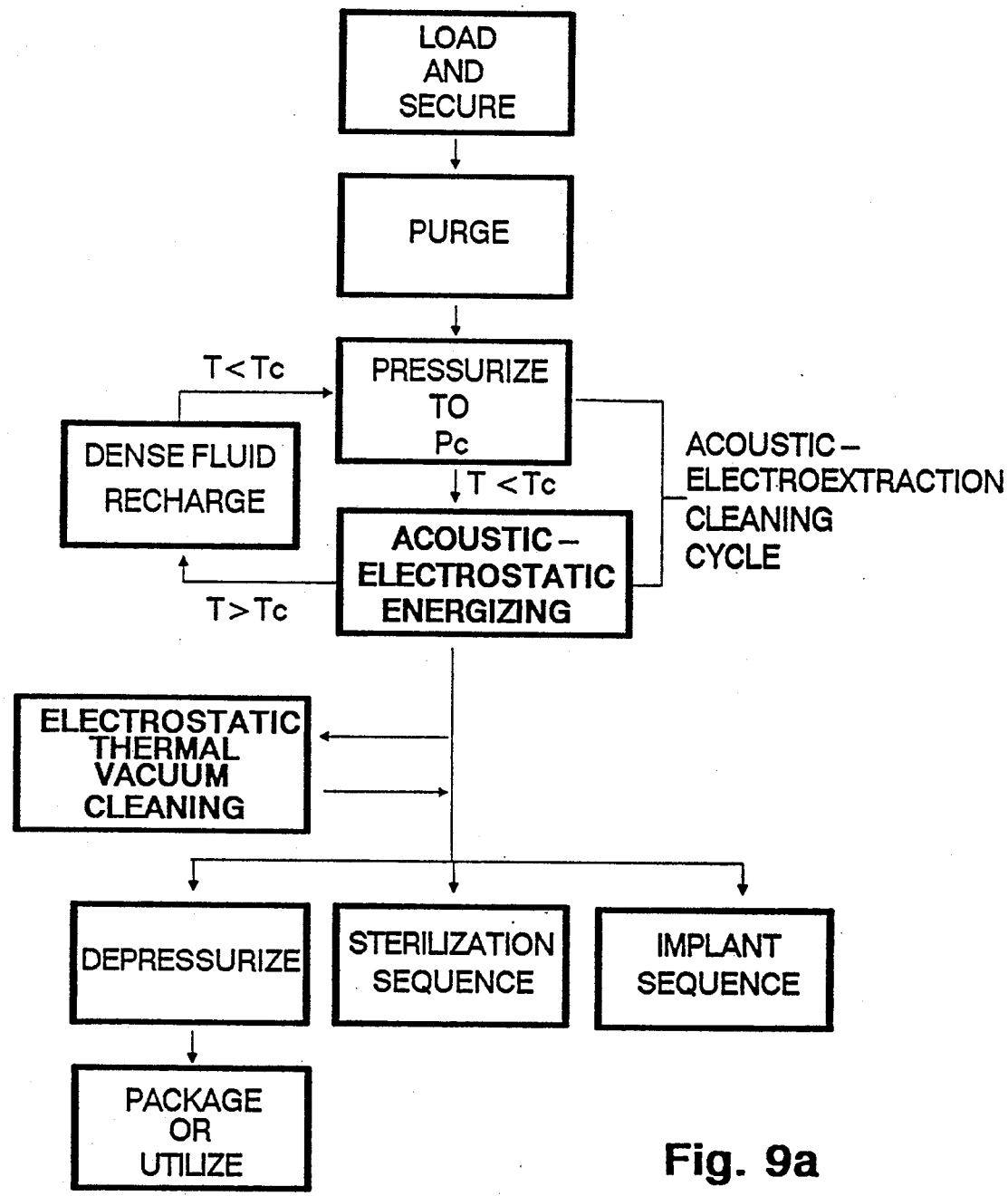
FIG. 9a, FIG. 9b, and FIG. 9c are flowcharts setting forth the cleaning, sterilization, and implanting processes, respectively, in accordance with the present invention.

A flowchart showing the steps in the material cleaning phase of the present invention is shown in FIG. 9a. The process is carried out in the cleaning and sterilization chamber which contains the material to be processed secured in the exemplary material loading rack, and the entire cleaning and sterilization system protected in a particle clean and sterile environment using an environmental control enclosure. As shown in FIG. 9a, a material is first loaded and secured in the exemplary cleaning and sterilization chamber, whereupon the cleaning and sterilization chamber is sealed using the preferred closure 86, FIG. 6a, purged for several minutes with helium or nitrogen, and followed with a 2 to 3 minute purge with the selected processing gas at a pressure of 10 to 100 atm. Gas purging removes volatile impurities such as moisture in the chamber and preconditions the material prior to pressurization to the operating pressures at or above the critical pressure for the selected processing gas or gas mixture. Following purging cycles, the chamber is pressurized to the critical pressure with the selected processing gas or gas mixture at a temperature below the critical temperature of the dense gas or gas mixture. The material is then simultaneously subjected to the acoustic and electrostatic energy cycles, shown in FIG. 4a and FIG. 4b respectively. During acoustic-electroextraction cycles, the internal chamber temperature is held below the critical temperature for the dense fluid using the internal temperature compensator 94, FIG. 6a, for several minutes. Subsequently, the internal temperature is allowed to rise to the critical temperature for the dense fluid or dense fluid mixture, whereupon the acoustic energy source is stopped and the chamber is recharged with preconditioned dense fluid at a pressure equal to or greater than the critical pressure. The alternating non-uniform electric field generator 56, FIG. 5, is on continuously during the cleaning and sterilization sequences. The acoustic-electroextraction and dense fluid recharge process is repeated as required to attain the desired cleanliness level, based on predetermined performance testing or based upon data from in-line real time chamber fluid testing such as supercritical gas chromatography. Following the pre-cleaning acoustic-electroextraction sequence, the chamber may be depressurized to ambient pressure (1 atm) or the sterilization or implant sequences may be initiated.

Figure 9B:
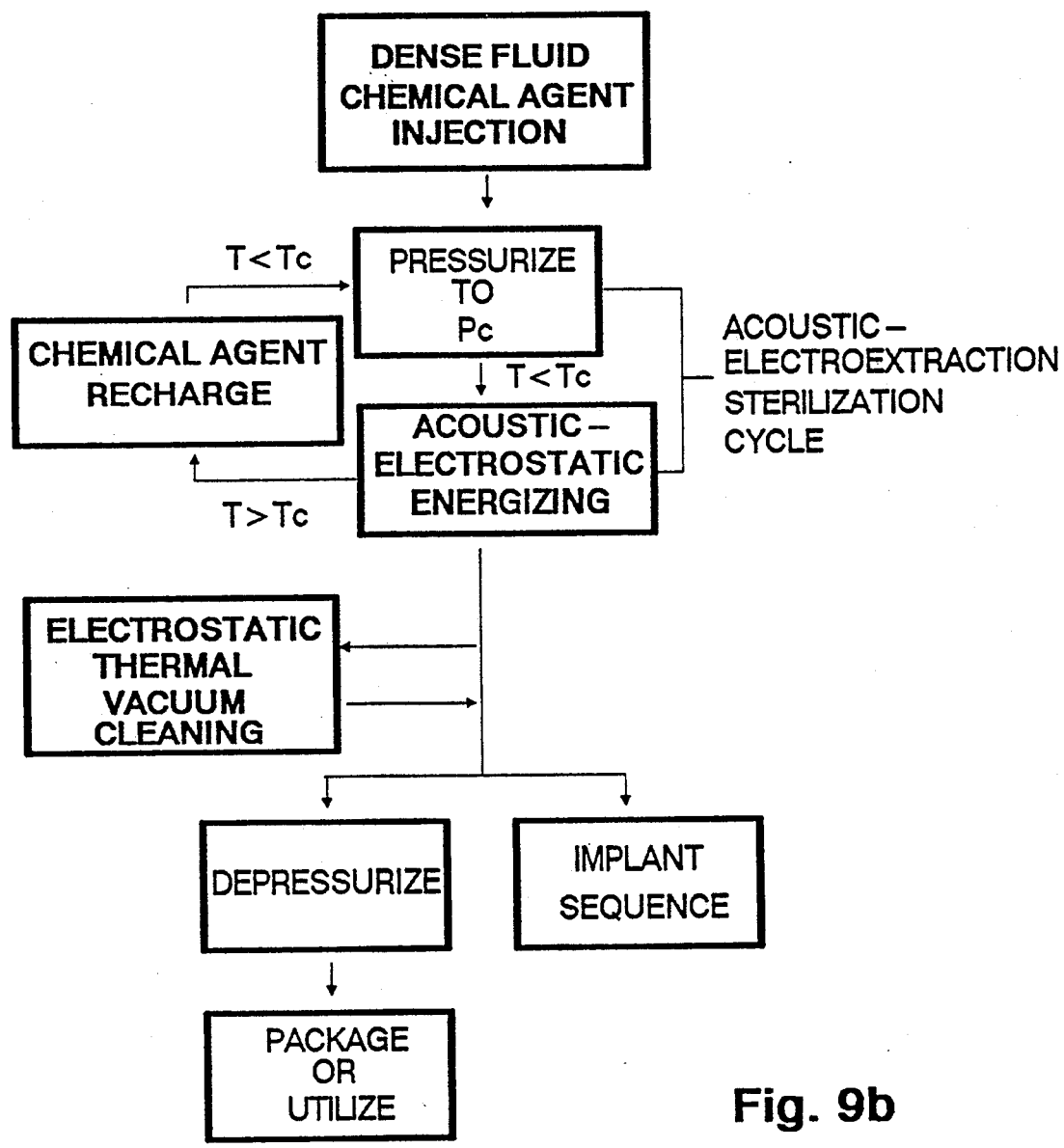

A flowchart showing the steps in the material sterilization phase is shown in FIG. 9b. The process is carried out in the same chamber as in the cleaning sequence above. As shown in FIG. 9b, the chamber is recharged with a dense fluid mixture of carbon dioxide and hydrogen peroxide or other suitable chemical agent admixture delivered via the chemical agent injection system exhaust port 120, FIG. 6b, and allowed to contact the material for several minutes. Following this, the acoustic-electroextraction cycles are repeated as described in the cleaning sequence above, using periodic chemical agent admixture recharges, until material sterility levels ar achieved. The frequency of chemical agent recharges is based upon experimentation, but at least one chemical agent recharge per acoustic-electroextraction cycle is required due to the rapid breakdown of dense fluid oxidizers such as hydrogen peroxide under the high energy conditions employed.

Following the material sterilization phase, the chamber is recharged with dense fluid to remove chemical agent residuals and then purged with nitrogen or helium for several minutes. The cleaning chamber and material are then depressurized to ambient by slowly exhausting the dense fluid and residual gas through the exhaust port 84, FIG. 6a. Alternatively, the cleaning and sterilization chamber may remain pressurized with dense fluid(s) for subsequent chemical implant operations. Alternatively, in accordance with the fifth embodiment of the present invention, argon gas is introduced into the cleaning chamber following cleaning and sterilization sequences at a vacuum pressure of 0.0001 Torr and 60 degrees celsius. Pulsed electrostatic energy is applied to ionize the argon environment to facilitate removal of residual volatile contaminants. Periodically, the cleaning chamber is recharged with preconditioned argon gas.

Following the first two processing sequences, preservatives or other chemical agents may be implanted in the clean and sterile material to provide long-term protection against biological contamination or to provide material property enhancements such as improved electrical insulation. In accordance with the sixth embodiment of the present invention, chemical agents such as biocides may be carried into the cleaning chamber, by suitable dense carrier fluids, from the chemical injection system and implanted in the material using a process called acoustic deposition in this invention.

Figure 9C:
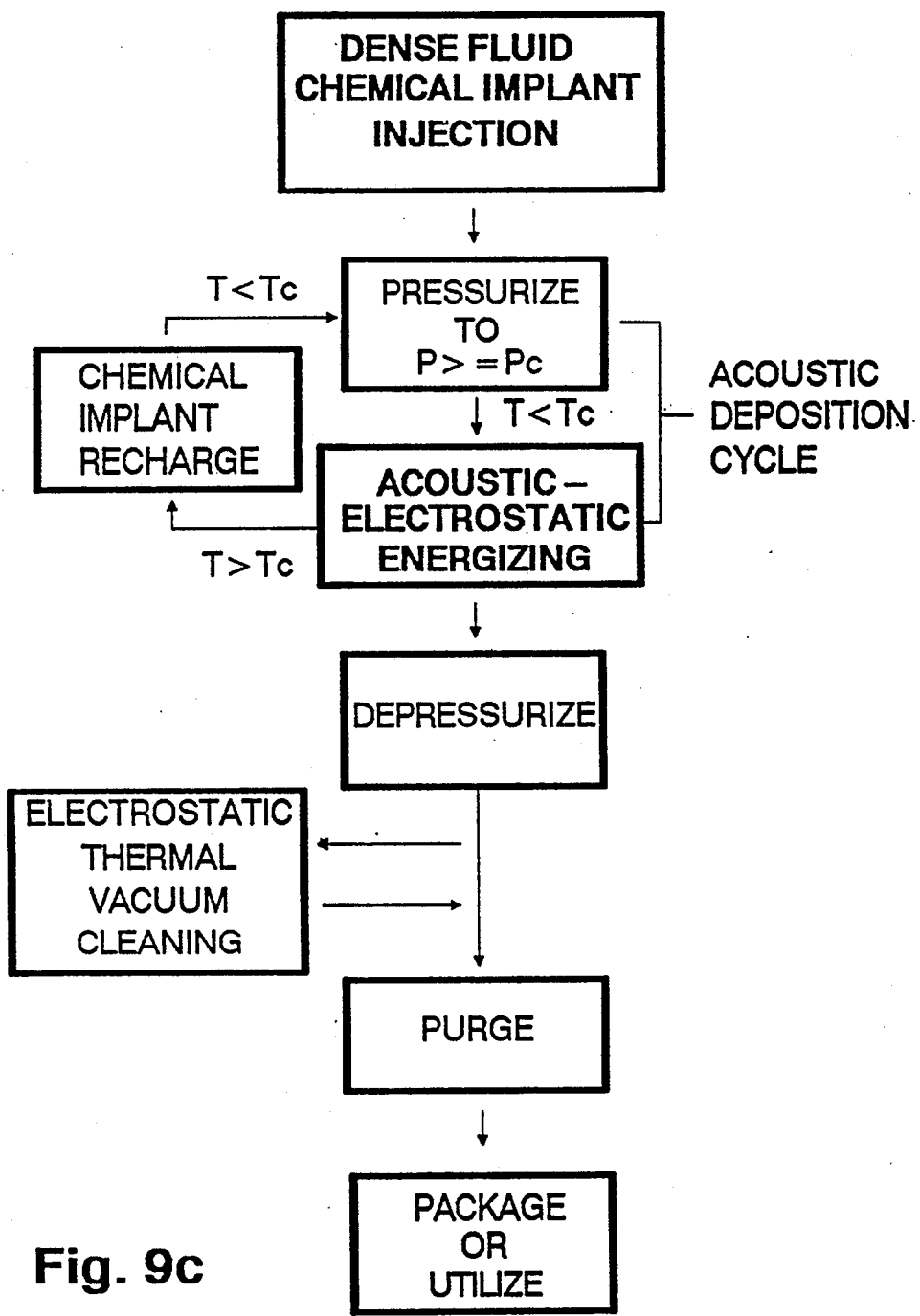

A flowchart showing the steps in the implant or acoustic deposition sequence is shown in FIG. 9c. The process is carried out in the same cleaning and sterilization chamber as the sterilization sequence above. As shown in FIG. 9c, a mixture of dense phase gas and chemical agent are injected into the cleaning and sterilization chamber at a pressure equal to or greater than the critical pressure and a temperature less than the critical temperature for the injection mixture, whereupon the mixture is allowed to contact and bathe the material for several minutes to assure homogeneous distribution in the process chamber and within the material. Following the contact period, the acoustic and electrostatic energy sources are simultaneously cycled as described in FIG. 4a and FIG. 4b without internal temperature control. The internal chamber fluid mixture temperature rises rapidly to the critical temperature during energizing, lowering the total cohesive energy content (solubility chemistry) of the dense carrier fluid(s), whereupon a fraction of the chemical agent is deposited on internal and external material surfaces. As previously discussed, the level and rate of chemical agent deposition can be controlled by adjusting the processing pressure, that is, the pressure at which the acoustic energy source is first initiated above the critical pressure. In addition, pulsing or adjusting power output on the acoustic amplifier can be used to control the level and rate of chemical agent deposition. Finally, depending upon the differences in the solubility chemistries at various temperatures, the internal temperature compensator 94, FIG. 6*a*, can be fed coolants or heating agents to adjust the temperature of the dense fluid-chemical agent admixture prior to or during acoustic-electrostatic energy cycles. Once the critical temperature for the dense fluid-chemical agent admixture is attained, the acoustic and electrostatic energy sources are shut down. The dense fluid-chemical admixture is then cooled down below the critical temperature using the internal closed-loop temperature compensator 94, FIG. 6*a*. Once the desired temperature is reached, dependant upon the solubility chemistry of the chemical agent and dense fluid(s), the coolant feed to the temperature compensator is stopped and the acoustic-electrostatic energy cycles are again initiated. Using this temperature and energy controlled sequence, the chemical agent is impregnated and deposited onto internal material surfaces in discrete coatings or layers. The cleaning and sterilization chamber is recharged with dense fluid-chemical agent admixture and the acoustic deposition cycle described above is repeated to achieve the desired deposition level. Once the required level of chemical agent is implanted in the material, the chamber is depressurized to ambient pressure (1 atm) and purged with preconditioned nitrogen or helium. The material may then be removed from the chamber, packaged, or used as desired. In accordance with the second embodiment of the present invention, materials may be prepackaged in semi-permeable membranes and implanted with chemical agents according to the processes described above.

In accordance with the fifth embodiment of the present invention, argon gas is introduced into the cleaning chamber at a vacuum pressure of 0.0001 Torr and 60 degrees C. Pulsed electrostatic energy is applied to ionize the argon environment to facilitate removal of residual volatile contaminants. Periodically, the cleaning chamber is recharged with pure argon gas.

Examples of practice of the present invention are as follows.

EXAMPLE 1

This example illustrates the use of one embodiment of the present invention to remove organic contaminants from liquid oxygen valves to prevent detonation during use. Oxygen valves may be contaminated with organics and inorganics such as oils and particulates. If not removed from these critical devices, they may lead to faulty operation of the valve seals or oxygen-contaminant detonation in the valve body when actuated. A dense phase carbon dioxide and hydrogen peroxide mixture (90:10) is used in combination with acoustic and electrostatic energy cycles to precision clean the material. The valves were loaded and secured in the cleaning and sterilization chamber and purged with preconditioned nitrogen gas at 10 atm for several minutes. Following gas purging, the chamber was pressurized with a 90:10 v:v mixture of carbon dioxide and hydrogen peroxide to a pressure of 150 atm at 25 degrees celsius. The valves were allowed to contact the mixture for several minutes, whereupon the acoustic energy source was initiated at 20 kilohertz and approximately 250 watts of input power on the titanium horn and the ion emitter plate was pulsed at +5000 volts/cm DC and −5000 volts/cm DC over 10 second intervals. This continued until the internal temperature increased to 35 degrees celsius, whereupon the energy sources were shut down and the chamber was depressurized to purge the chamber of extracted contaminants and recharged with dense carbon dioxide-hydrogen peroxide as above. The process above was repeated several times over 20 minutes. Following the acoustic-electroextraction cycles, the chamber was recharged with a dense phase carbon dioxide at 150 atm and 25 degrees celsius and the acoustic-electorextraction cycles were repeated as above, with periodic recharges of dense phase carbon dioxide, to remove residual hydrogen peroxide and supercritical oxidation by-products. Following this, the chamber was purged with preconditioned argon and the chamber was depressurized to 0.0001 Torr using a high vacuum pump and heated to 60 degrees celsius using an external ceramic band heater. A voltage of +5000 volts/cm DC and −5000 volts/cm DC was applied to the ion emitter plate (the ion collector plate was grounded in series with the electrostatic generator) and the internal temperature compensator (ion collector plate) was cooled to less than −50 degrees celsius with liquid nitrogen for 30 minutes. Following thermal electrostatic vacuum operations, the chamber pressure was returned to 1 atm with preconditioned nitrogen. Subsequent hexane solvent extractions of the miniature oxygen valves revealed no detectable hydrocarbon contaminants in the valves.

EXAMPLE 2

This example illustrates the use of the cleaning and sterilization processes of the present invention to clean titanium clips prepackaged in TYVEK semi-permeable membranes for use in attaching bone and tissue in surgical applications. A cleaning and sterilization sequence identical to the process carried out in example 1 with a 2% v:v loading of hydrogen peroxide resulted in visibly clean titanium clips and a negative bacterial count upon processing the clean and sterile titanium clips according to standard microbiological culturing techniques.

EXAMPLE 3

This example illustrates the use of cleaning and sterilization processes of the present invention to clean dentures. In accordance with the cleaning and sterilization processes of the present invention, a dense phase carbon dioxide, nitrous oxide, and sodium 2-ethylhexyl sulfate (Surfactant/Penetrant) at a ratio of approximately 85:10:5 v:v, respectively, was acoustically and electrostatically radiated in several cycles at 150 atm and 25 celsius. The critical temperature for nitrous oxide is approximately 37 degrees celsius, therefore, the mixture was energized according to the acoustic-electroextraction cycles of the present invention until a temperature of the mixture reached 40 degrees celsius, whereupon the mixture was exhausted and the chamber was recharged and reenergized. Following this, a mixture of dense phase carbon dioxide and hydrogen peroxide 90:10 v:v at 150 atm and 25 degrees celsius was used in several acoustic-electroextraction cycles to extract residual organic contaminants and to provide deep sterilization. Following processing, the dentures were visibly clean and bacterial culturing tests revealed no microbiological growth.

EXAMPLE 4

This example illustrates the use of cleaning, sterilization, and chemical implant processes of the present invention to prepare a silicone voice prosthesis for biological use. A silicone voice prostheses was cleaned and sterilized in a procedure identical to example 2 except that following cleaning and sterilization sequences using the high energy carbon dioxide-hydrogen peroxide mixture, n-octyl alcohol was implanted according to the implant process described above. Microbiological culturing tests on representative portions of the silicone prosthesis revealed no biological activity several weeks following the implant process.

The processes of the present invention have numerous material cleaning, sterilization, and chemical implant applications. A wide variety of materials can be prepared for biomedical, aerospace, and high energy environments where material cleanliness and sterility are a concern, including biomaterials, prostheses, precision and miniature valves, surgical textiles, and surgical application aids. The particular processing parameters employed using the processes herein will vary depending upon the nature of the material, the type of contaminants to be removed, and level of cleanliness and sterility desired. This process is well suited to preparing materials having complex and intricate internal and external geometries and having many different construction materials.

Having thus described exemplary embodiments of the present invention, it should be noted by those skilled in the art that the within disclosures are exemplary only and that various other alternatives, adaptations, or modifications may be made within the scope of the present invention. Accordingly, the present invention is not limited to the specific embodiments as illustrated herein, but is only limited by the following claims.

What is claimed is:

1. A process for removing two or more contaminants from a substrate surface comprising the steps of:
   a) placing said substrate containing said contaminants in a cleaning, sterilization, and implant chamber; and
   b) contacting said substrate containing said contaminants with a dense fluid at a pressure equal to or above the critical pressure of a said dense fluid; and
   c) simultaneously subjecting said dense fluid to a high energy source of acoustic radiation and a non-uniform electrostatic energy field, and maintaining contact of said energized dense fluid with said substrate containing said contaminants for a predetermined period of time above the critical pressure and below critical temperature of said dense fluid, wherein contaminant solubility and transport from said substrate is provided to thereby remove said two or more contaminants from said substrate in one continuous process; and adding a chemical agent to the dense fluid;
   d) simultaneously subjecting said dense fluid and said chemical agent dissolved in said dense fluid to a high energy source of acoustic radiation and a non-uniform electric field, and contacting said substrate for a predetermined period of time with said energized dense fluid, and increasing temperature of said dense fluid to the critical temperature for said dense fluid, wherein said substrate is coated with said chemical agent.

2. The process as set forth in claim 1 wherein said high energy acoustic radiation is applied to said dense fluid with temperature below its critical temperature.

3. The process as set forth in claim 1 wherein the temperature of said dense fluid is allowed to rise to the critical temperature or above and then decreasing said temperature for a few minutes to below the critical temperature.

4. The process as set forth in claim 1 wherein said acoustic energy is pulsed between 200 and 400 watts over several minutes.

5. The process as set forth in claim 4 wherein said acoustic energy is varied between 20 and 40 kilohertz.

6. The process as set forth in claim 1 wherein said acoustic radiation is stopped once the critical temperature for said dense fluid has been reached.

7. The process as set forth in claim 1 wherein said non-uniform electrostatic field is derived from a combination of a charged plate which is parallel with a smaller and oppositely charged plate separated by a finite distance.

8. The process as set forth in claim 7 wherein said non-uniform electrostatic field is charged to between +10,000 volts/cm DC and 10,000 volts/cm DC.

9. The process as set forth in claim 8 wherein said non-uniform electrostatic field is on continuously under high vacuum and moderate temperatures to improve volatile contaminant removal.

10. The process as set forth in claim 1 wherein said non-uniform electrostatic field is continuous during acoustic operation.

11. The process as set forth in claim 1 wherein said dense fluid is selected from the group consisting of carbon dioxide, nitrous oxide, krypton, xenon, argon, oxygen, helium, nitrogen, ammonia, and mixtures thereof.

12. The process as set forth in claim 11 wherein said dense fluid is selected from a mixture of carbon dioxide and nitrous oxide.

13. The process as set forth in claim 11 wherein said dense fluid is mixed with a chemical agent to improve dense fluid cleaning effectiveness.

14. The process as set forth in claim 13 wherein said chemical agent is selected from a group consisting of organo-metallics, biocides, surfactants, alcohols, dyes, oxidizers, and odorants.

15. The process as set forth in claim 13 wherein said dense fluid and chemical agent mixture consist of liquidifed carbon dioxide and hydrogen peroxide.

16. The process as set forth in claim 1 wherein said dense fluid is mixed with a chemical agent and said chemical agent is deposited on said substrates.

17. The process as set forth in claim 16 wherein said chemical agent changes performance properties of said dense fluid.

18. The process as set forth in claim 1 wherein said substrate comprises material selected from a group consisting of metal, wood, rubber, and ceramics.

19. The process as set forth in claim 18 wherein said substrate is selected from a group consisting of prostheses, and dental implant.

20. The process as set forth in claim 1 wherein said contaminant is selected from a group consisting of bacteria, spores, and plasticizer.

* * * * *